United States Patent
Richards

(10) Patent No.: US 12,168,109 B1
(45) Date of Patent: Dec. 17, 2024

(54) BOOTH FOR APPLICATION OF TANNING FLUIDS

(71) Applicant: Melanie Jane Richards, Eden Prairie, MN (US)

(72) Inventor: Melanie Jane Richards, Eden Prairie, MN (US)

( * ) Notice: Subject to any disclaimer, the term of this patent is extended or adjusted under 35 U.S.C. 154(b) by 0 days.

(21) Appl. No.: 18/421,902

(22) Filed: Jan. 24, 2024

(51) Int. Cl.
| A61M 35/00 | (2006.01) |
| B05B 14/43 | (2018.01) |
| B05B 16/40 | (2018.01) |
| B05B 16/60 | (2018.01) |

(52) U.S. Cl.
CPC .............. *A61M 35/25* (2019.05); *B05B 14/43* (2018.02); *B05B 16/405* (2018.02); *B05B 16/60* (2018.02)

(58) Field of Classification Search
CPC ....... B05B 14/43; B05B 16/405; B05B 16/60; B05B 16/00; A61M 35/25; A61M 11/00; A61M 37/00; A45D 34/00; A45D 2200/057; A01K 13/003; B05C 15/00
See application file for complete search history.

(56) References Cited

U.S. PATENT DOCUMENTS

| 2,708,829 | A | * | 5/1955 | Heinrich | .............. | D01H 11/005 |
| | | | | | | 57/304 |
| 6,302,122 | B1 | | 10/2001 | Parker et al. | | |
| 6,554,208 | B1 | | 4/2003 | Venuto, Sr. | | |
| 7,004,932 | B2 | | 2/2006 | Szurko | | |
| 7,462,242 | B2 | | 12/2008 | Cooper et al. | | |
| 8,201,288 | B2 | | 6/2012 | Thomason et al. | | |
| 2004/0147884 | A1 | * | 7/2004 | Szurko | .................... | B05B 14/46 |
| | | | | | | 604/289 |
| 2010/0001097 | A1 | | 1/2010 | Spivak | | |
| 2015/0125409 | A1 | | 5/2015 | Marling et al. | | |

OTHER PUBLICATIONS

Minetan Body. Skin, All In One Tan Booth <https://US.shop.minetanbodyskin.com/collections/professional-spray-tan-equipment/products/all-in-one-spray-tan-booth> date accessed Apr. 17, 2024, reviews going back 2 years and wayback machine screen shot from 2020. (Year: 2020).*
YouTube How to Put Together the All in One Tan |MineTan Professional <https://www.youtube.com/watch?v=m7D6mt95mA0> posted Jan. 10, 2022. (Year: 2022).*
Tan. Booth. Extraction Operational Manual uploaded Jun. 2019 <https://minetanbodyskin.com/wp-content/uploads/2019/06/Tan.Booth-Manual.pdf> (Year: 2019).*
All in One Tan.Booth | EXTRACTION + Spray Tan Machine | Product Data & Assembly Guide Mine, Tan.Body.Skin MarqLabs, 291 Edgewood Street, Alexandria. TN. 37012 (Year: 2019) | pp. 5 minetanbodyskin.com.
Tan. Easy Pro Tools Operation Manual www.taneasyprotools.com.

* cited by examiner

*Primary Examiner* — Benjamin J Klein
*Assistant Examiner* — Gabriella E Burnette
(74) *Attorney, Agent, or Firm* — Fargo Patent & Business Law; Thomas Kading

(57) ABSTRACT

A booth for application of tanning fluid according to one disclosed non-limiting embodiment of the present disclosure includes a semi-cylindrical enclosure which comprises a floor and a curved wall; a vent system in the curved wall; and a multiple of fans to collect tanning fluid overspray through the vent system, the multiple of fans arranged transverse to the vent system.

9 Claims, 5 Drawing Sheets

BOOTH FOR APPLICATION OF TANNING FLUIDS

CROSS REFERENCE TO RELATED APPLICATION[S]

None

BACKGROUND

The present disclosure relates to an overspray collection booth, and more specifically, to the collection of tanning fluid overspray during the application of tanning fluid to the human body.

Sun-tanned skin is often found to be attractive. People often spend significant time exposing their skin to the sun to obtain a tan. However, over the last several decades, people have been seeking other ways of obtaining the look of sun-tanned skin while avoiding prolonged exposure to the sun. One of the ways people have found to obtain the look of sun-tanned skin is by applying tanning fluids to their skin that bestows the look of sun-tanned skin.

One of the more popular ways of applying tanning fluids is to airbrush the tanning fluids onto the skin. During the application of the tanning fluids, overspray tends to surround the person and some tanning fluids at certain concentrations may not be approved by the FDA for inhalation.

SUMMARY

A booth for application of tanning fluid according to one disclosed non-limiting embodiment of the present disclosure includes a semi-cylindrical enclosure which comprises a floor and a curved wall; a vent system in the curved wall; and a multiple of fans to collect tanning fluid overspray through the vent system, the multiple of fans arranged transverse to the vent system.

A further embodiment of any of the foregoing embodiments of the present disclosure includes, wherein the multiple of fans comprise four fans.

A further embodiment of any of the foregoing embodiments of the present disclosure includes, wherein the multiple of fans comprise four fans, two fans arranged with respect to a first vent panel of the vent system and two fans arranged with respect to a second vent panel of the vent system.

A further embodiment of any of the foregoing embodiments of the present disclosure includes, wherein the first vent panel is arranged vertically with respect to the second vent panel.

A further embodiment of any of the foregoing embodiments of the present disclosure includes a light system within the semi-cylindrical enclosure, the light system comprises a strip light arranged along each edge of the curved wall which flanks an opening to the booth.

A further embodiment of any of the foregoing embodiments of the present disclosure includes, wherein two of the multiple of fans form a downward directed airflow pattern and two of the multiple of fans form an upward directed airflow pattern.

A booth for application of tanning fluid according to one disclosed non-limiting embodiment of the present disclosure includes a semi-cylindrical enclosure which comprises a floor and a curved wall; a vent system in the curved wall; and a multiple of fans to collect tanning fluid overspray through the vent system, the multiple of fans arranged transverse to the vent system such that two of the multiple of fans form a downward directed airflow pattern and two of the multiple of fans form an upward directed airflow pattern.

The foregoing features and elements may be combined in various combinations without exclusivity, unless expressly indicated otherwise. These features and elements as well as the operation thereof will become more apparent in light of the following description and the accompanying drawings. It should be appreciated that however the following description and drawings are intended to be exemplary in nature and non-limiting.

BRIEF DESCRIPTION OF THE DRAWINGS

Various features will become apparent to those skilled in the art from the following detailed description of the disclosed non-limiting embodiment. The drawings that accompany the detailed description can be briefly described as follows.

DETAILED DESCRIPTION

Figure 1:
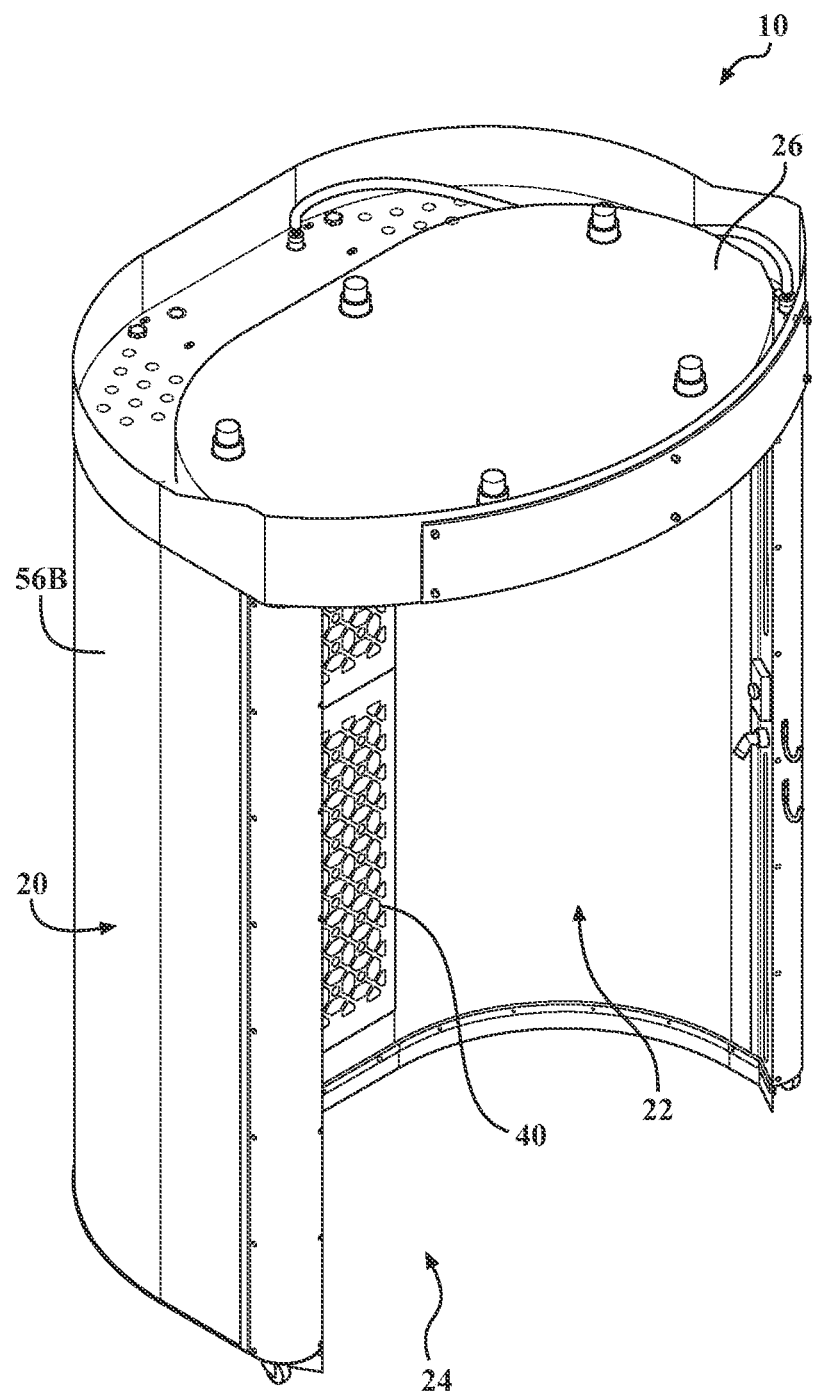
FIG. 1 is a left front perspective view of a booth for the collection of tanning fluid overspray according to one disclosed non-limiting embodiment.

FIG. 1 schematically illustrates a booth 10 for the collection of tanning fluid overspray that generally includes a semi-cylindrical enclosure 20 with a curved wall 22, and an overspray collection system 30 (FIGS. 2A and 2B) in communication with a vent system 40 in the curved wall 22. The booth 10 is especially designed to collect tanning fluid overspray during the application of tanning fluid by a manually operated airbrush device. The tanning fluid overspray may include, for example, pre-tan ph balancing spray, sunless tanning solution, post tan moisturizing spray, powders, and/or other sprays that are applied to the client's skin while the client stands within the booth 20.

Figure 3:
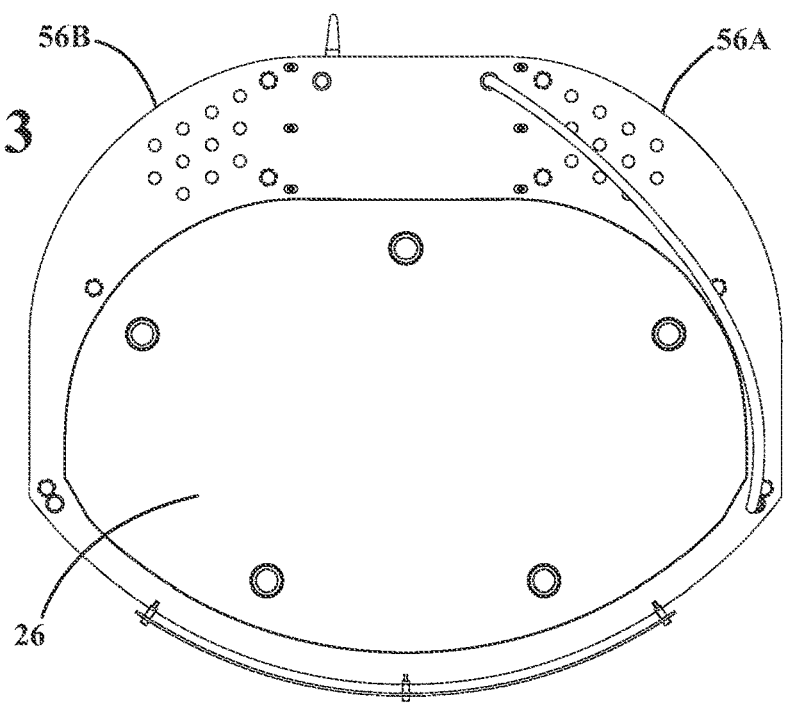
FIG. 3 is a top view of the booth for the collection of tanning fluid overspray according to another disclosed non-limiting embodiment.

The semi-cylindrical enclosure 20 may include the curved wall 22 to form a crescent-like shape with a walk-in opening 24. The semi-cylindrical enclosure 20 may include a generally ovaloid shaped ceiling 26 (FIG. 3). In one embodiment, the semi-cylindrical enclosure 20 may be 89 inches tall (FIG. 4) and the ceiling 26 may be about 63 inches by 54 inches (FIG. 3). The ceiling 26 may, for example, be detachable from the semi-cylindrical enclosure 20. Wheels may, for example, be attached to the semi-cylindrical enclosure 20 to facilitate repositioning of the booth 10.

Figure 4:
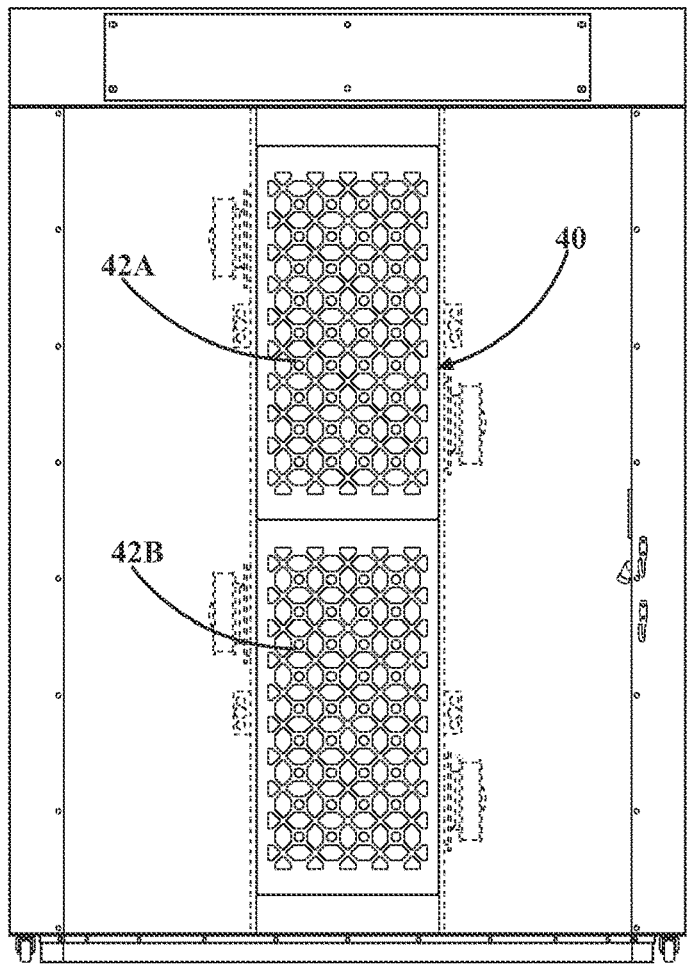
FIG. 4 is a front view of the booth for the collection of tanning fluid overspray according to another disclosed non-limiting embodiment.

The vent system 40 is located in the curved wall 22 directly opposite the walk-in opening 24. In one embodiment, the vent system 40 may be 80 inches tall and include a first vent panel 42A and a second vent panel 42B (FIG. 4). The curved wall 22 may include one or more slots with which the vent panels 42A, 42B engage. The vent panels 42A, 42B may be removably secured to the curved wall 22 with magnets.

Figure 2B:
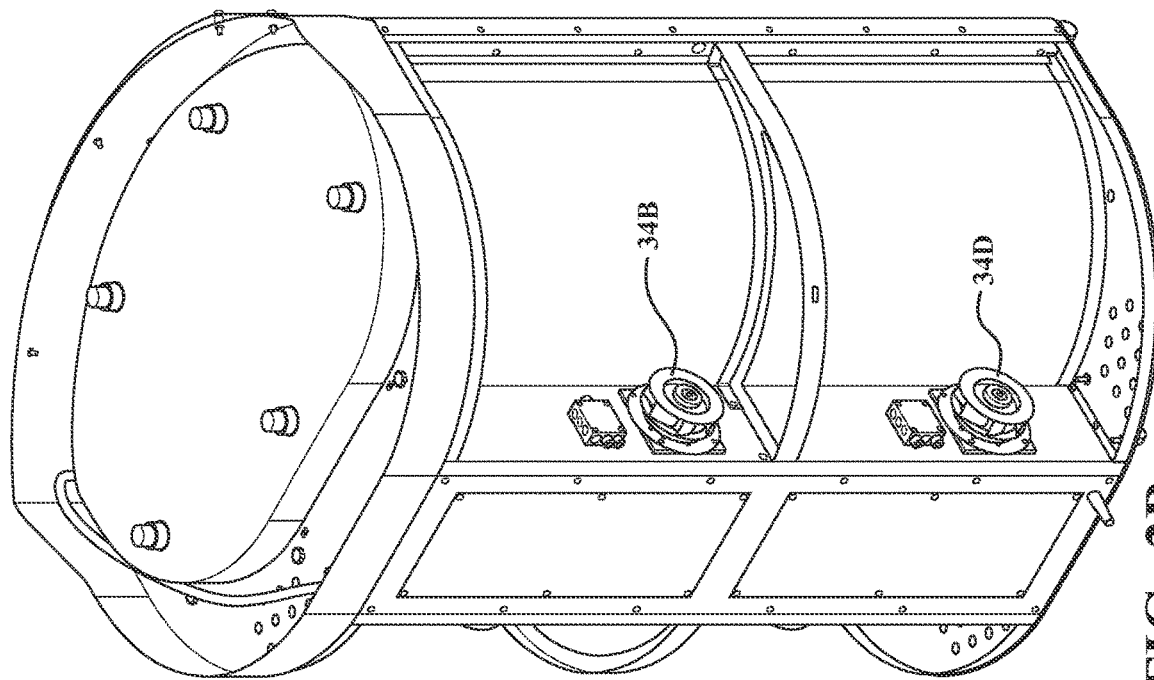
FIG. 2B is a left rear perspective view of the booth for the collection of tanning fluid overspray according to one disclosed non-limiting embodiment.
Figure 2A:
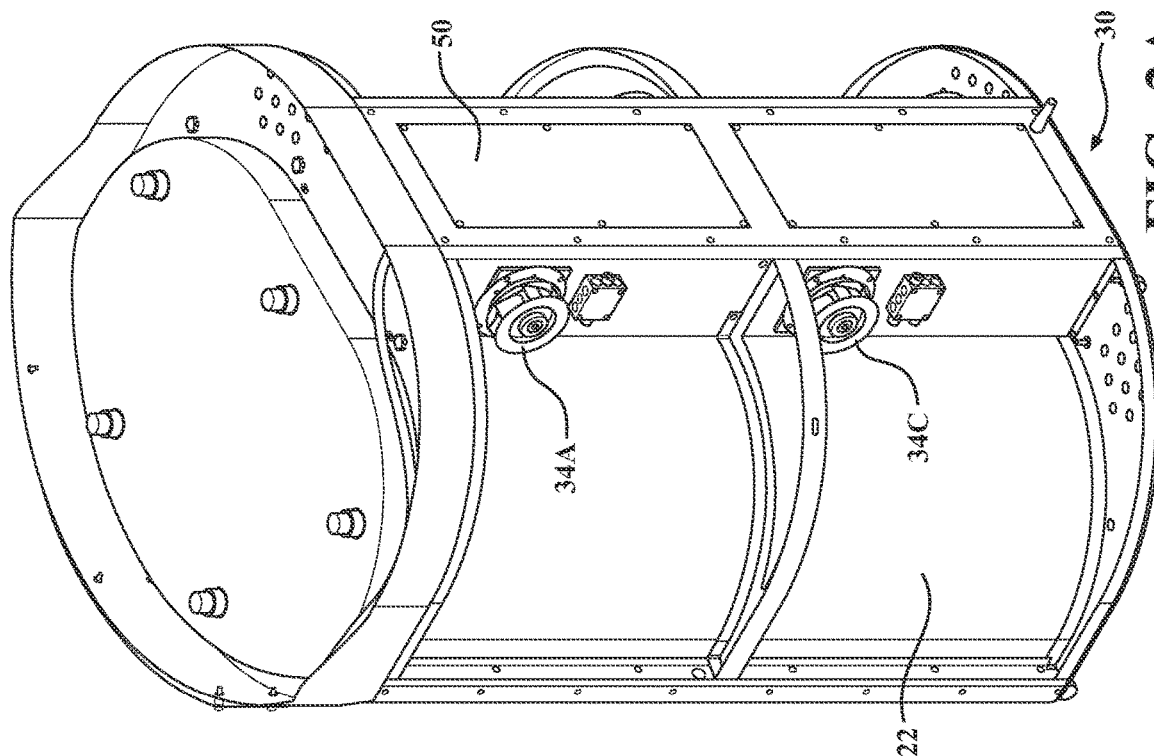
FIG. 2A is a right rear perspective view of the booth for the collection of tanning fluid overspray according to one disclosed non-limiting embodiment.

With reference to FIGS. 2A and 2B, the overspray collection system 30 may be located in a housing 50 located adjacent to the vent system 40 behind the curved wall 22 with respect to the walk-in opening 24. The overspray collection system 30 may include a multiple of fans (four shown 34A, 34B, 34C, 34D; FIGS. 2A and 2B). Each of the multiple of fans 34A, 34B, 34C, 34D may, for example, be variable speed. Two fans 34A, 34B may be arranged transverse with respect to the first vent panel 42A and two fans 34C, 34D may be arranged transverse with respect to the second vent panel 42B. More specifically, the two fans 34A, 34B may be perpendicular to the first vent panel 42A and the two fans 34C, 34D may be arranged perpendicular to the second vent panel 42B (FIG. 5).

Figure 5:
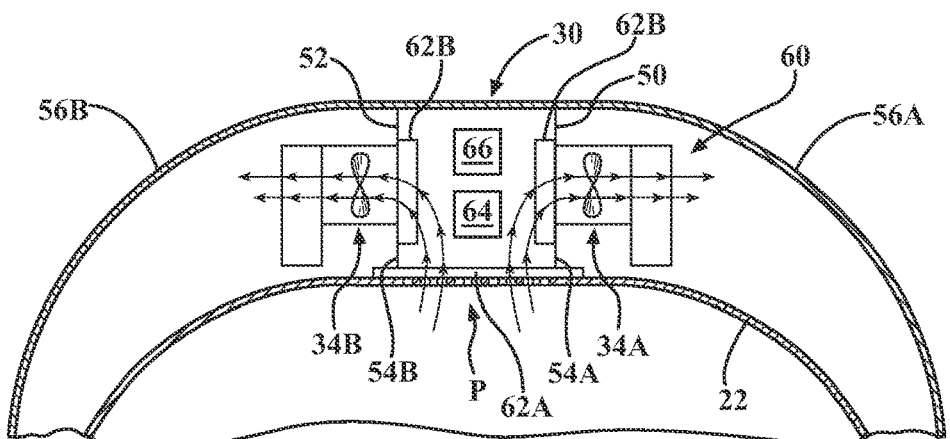
FIG. 5 is a top schematic view of the booth for the collection of tanning fluid overspray illustrating an airflow pattern.

With reference to FIG. 5, the housing 50 may include a rectilinear duct 52 adjacent to the vent system 40 behind the curved wall 22. The fans 34A, 34B, 34C, 34D are located in respective side walls 54A, 54B of the rectilinear duct 52. Removable curved rear walls 56A, 56A that interface with the rectilinear duct 52 provide an enclosure for the fans 34A, 34B, 34C, 34D and other accessory components 60 such as a filter system 62, compressor system 64, electrical controls 66, etc. The filter system 62 may include a vent filter 62A located aft of the vent system 40 as well as an in-line filter 62B located upstream of each fan 34A, 34B, 34C, 34D. The vent filter 62A may be, for example, 18×36×1 sure-fit 1-inch black poly foam, MERV8 which is perpendicular to each in-line filter 62B which may be, for example, 1-inch black poly foam, MERV8.

The filter system 62 may include at least one vent filter located behind the first vent panel 42A and the second vent panel 42B. The filter system 62 may include at least one in-line filter in line with each fan 34A, 34B, 34C, 34D. Filters used in the filter system may, for example, be of a Minimum Efficiency Reporting Value (MERV) of 8. Filters used in the filter system may, for example, be removable and/or cleanable.

Figure 6:
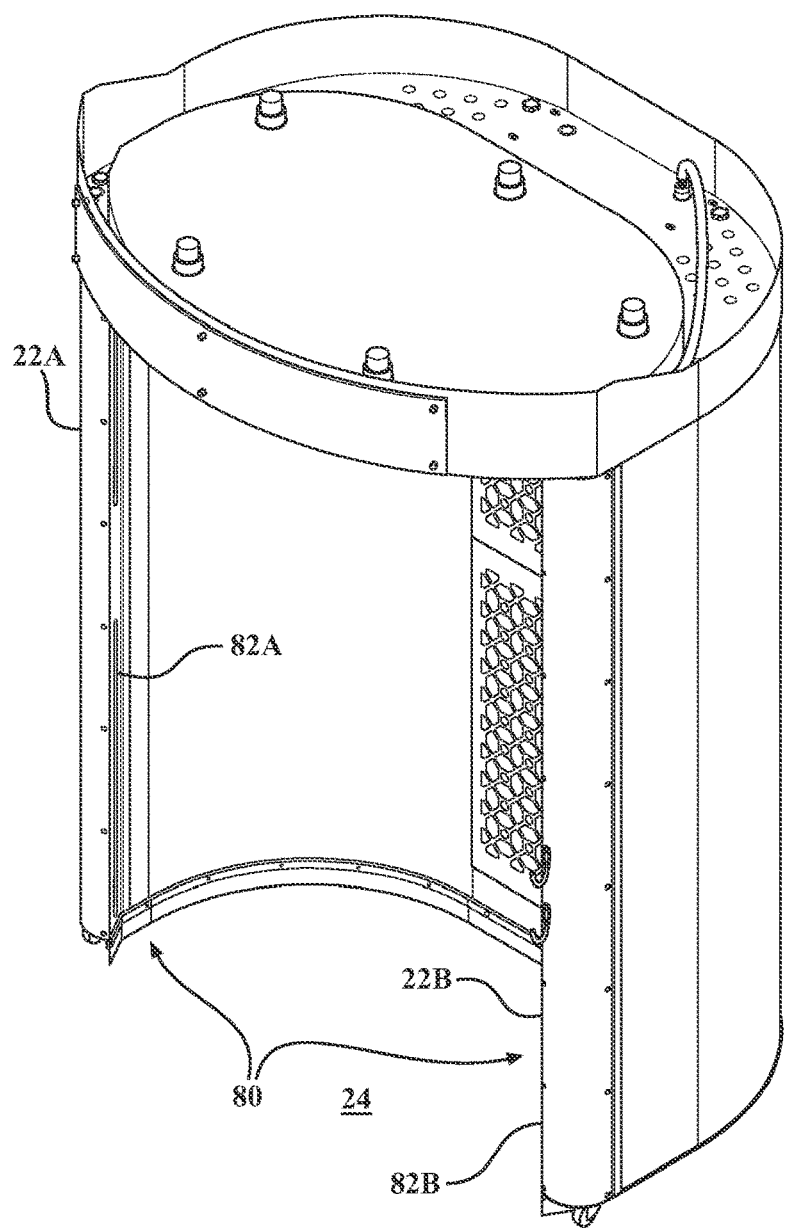
FIG. 6 is a right front perspective view of a booth for the collection of tanning fluid overspray according to one disclosed non-limiting embodiment.

With reference to FIG. 6, a light system 80 may include strip lights 82A, 82B arranged along each edge 22A, 22B of the curved wall 22 which flank the walk-in opening 24. The strip lights 82A, 82B may be LED lights that facilitate application of the tanning fluid as the client is illuminated. The light system 80 facilitates observation of the exact tone and texture of the client's skin by the technician to ensure an even application as well as being able to assess the client's natural skin tone for application of the correct solution.

Figure 7:
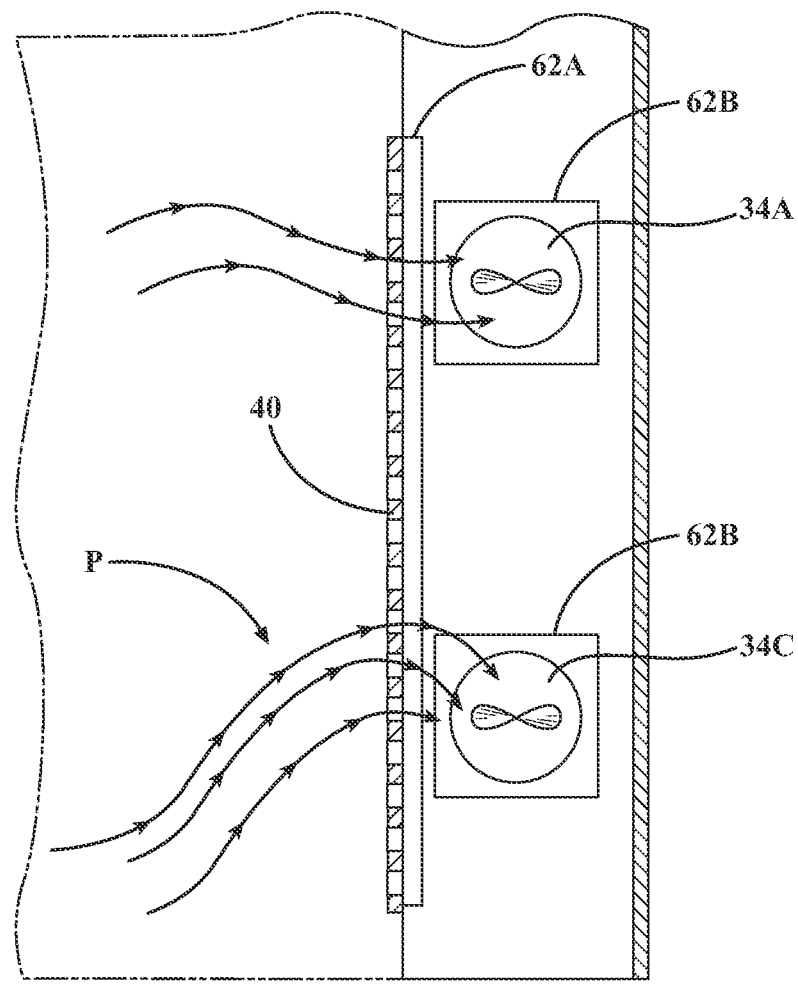
FIG. 7 is a side schematic view of the booth for the collection of tanning fluid overspray illustrating an airflow pattern.

In operation, the fans 34A, 34B, 34C, 34D are oriented to draw tanning fluid overspray though the vent system 40 and into the filter system 62. The orientation of the fans 34A, 34B forms a downward directed airflow pattern P (FIG. 7) within the booth 20 while the orientation of the fans 34C, 34D forms an upward directed airflow pattern P (FIG. 7). The downward directed airflow pattern P from the fans 34A, 34B safeguards the client so that the client will not breath the tanning fluid overspray while the upward directed airflow pattern P from the fans 34C, 34D avoids the heavier than air tanning fluid overspray from collecting onto the client's feet. The air flow pattern P results in a safe and more even application of the tanning fluid overspray to the client's skin.

Although the different non-limiting embodiments have specific illustrated components, the embodiments of this invention are not limited to those particular combinations. It is possible to use some of the components or features from any of the non-limiting embodiments in combination with features or components from any of the other non-limiting embodiments.

The foregoing description is exemplary rather than defined by the limitations within. Various non-limiting embodiments are disclosed herein, however, one of ordinary skill in the art would recognize that various modifications and variations in light of the above teachings will fall within the scope of the appended claims. It is therefore to be appreciated that within the scope of the appended claims, the disclosure may be practiced other than as specifically described. For that reason, the appended claims should be studied to determine true scope and content.

What is claimed is:

1. A booth for application of a heavier than air tanning fluid, comprising:
   a semi-cylindrical enclosure which comprises a floor and a curved wall to form a walk-in opening;
   a vent system in the curved wall, the vent system comprises a first vent panel arranged vertically above a second vent panel with respect to the floor;
   a housing aft of the vent system with respect to the curved wall with respect to the walk-in opening;
   a first fan mounted to the housing transverse to the first vent panel to form a downward directed airflow pattern with respect to the floor such that a client will not breath in a heavier than air tanning fluid overspray;
   a second fan mounted to the housing transverse to the first vent panel to form a downward directed airflow pattern with respect to the floor such that the client will not breath in the heavier than air tanning fluid overspray;
   a third fam mounted to the housing transverse to the second vent panel to form an upward directed airflow pattern with respect to the floor such that the heavier than air tanning fluid overspray will not collect on the client's feet;
   a fourth fan mounted to the housing transverse to the second vent panel to form an upward directed airflow pattern with respect to the floor such that the heavier than air tanning fluid overspray will not collect on the client's feet;
   a first vent filter located aft of the first vent panel perpendicular to the first and second fan;
   a second vent filter located aft of the second vent panel perpendicular to the third and fourth fan;
   a first in line filter mounted to the housing upstream of the first fan;
   a second in line filter mounted to the housing upstream of the second fan;
   a third in line filter mounted to the housing upstream of the third fan; and
   a fourth in line filter mounted to the housing upstream of the fourth fan.

2. The booth as recited in claim 1, further comprising a light system within the semi-cylindrical enclosure, the light system comprises a strip light arranged along each edge of the curved wall which flanks the walk-in opening to the booth.

3. The booth as recited in claim 1, wherein the semi-cylindrical enclosure forms a crescent shape.

4. The booth as recited in claim 1, wherein the first fan is vertical offset from the second fan with respect to the floor.

5. The booth as recited in claim 4, wherein the third fan is vertical offset from the fourth fan with respect to the floor.

6. The booth as recited in claim 1, further comprising an overspray collection system located aft of the vent system behind the curved wall with respect to the walk-in opening, the overspray collection system formed by the housing, a first removable curved rear wall, and a second removable curved rear wall to form a crescent shaped cavity aft of the curved wall.

7. The booth as recited in claim 6, wherein the housing comprises a rectilinear duct aft of the vent system behind the curved wall with respect to the walk-in opening, the first removable curved rear wall and the second removable curved rear wall attachable to the rectilinear duct.

8. The booth as recited in claim 6, wherein the first, second, third and fourth in line filter is located within the housing.

9. The booth as recited in claim 8, further comprising electrical controls located within the housing.

\* \* \* \* \*